(12) United States Patent
Domon et al.

(10) Patent No.: US 7,348,416 B2
(45) Date of Patent: Mar. 25, 2008

(54) SELECTIVE CAPTURE AND ENRICHMENT OF PROTEINS EXPRESSED ON THE CELL SURFACE

(75) Inventors: Bruno Domon, Rockville, MD (US); Ian McCaffery, Rockville, MD (US); Terence Ryan, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 144 days.

(21) Appl. No.: 10/992,235

(22) Filed: Nov. 19, 2004

(65) Prior Publication Data

US 2006/0154332 A1    Jul. 13, 2006

Related U.S. Application Data

(60) Provisional application No. 60/523,696, filed on Nov. 21, 2003.

(51) Int. Cl.
*A23J 1/00* (2006.01)
(52) U.S. Cl. ..................................... 530/413
(58) Field of Classification Search .................. 514/12
See application file for complete search history.

(56) References Cited

U.S. PATENT DOCUMENTS

| | | | |
|---|---|---|---|
| 6,335,155 | B1 | 1/2002 | Wells et al. |
| 6,670,194 | B1 | 12/2003 | Aebersold et al. |
| 2002/0022233 | A1 | 2/2002 | Wells et al. |
| 2002/0081621 | A1 | 6/2002 | Wells et al. |
| 2002/0119490 | A1 | 8/2002 | Aebersold et al. |
| 2003/0077826 | A1 | 4/2003 | Edelman et al. |
| 2004/0023306 | A1 | 2/2004 | Aebersold et al. |

OTHER PUBLICATIONS

Zimmer et al., N-Glycans of F Protein Differentially Affect Fusion Activity of Human Respiratory Syncytial Virus, J. of Virology, May 2001, p. 4744-4751.*

Zhang, et al., "Identification and Quantification of N-Linked Glycoproteins Using Hydrazide Chemistry, Stable Isotope Labeling and Mass Spectrometry", Nature Biotechnology, vol. 21, pp. 660-666, Jun. 2003.

* cited by examiner

*Primary Examiner*—Kathleen Kerr Bragdon
*Assistant Examiner*—Agnes Rooke
(74) *Attorney, Agent, or Firm*—Lin Sun-Hoffman

(57) ABSTRACT

The present invention provides a method for enriching cell surface proteins by oxidizing glycosylated protein with periodate. The present invention further provides that the cell surface proteins are obtained from intact cells either from cell lines or from tissues. The present invention provides a method not only capable of obtaining increased quantities of the cell surface proteins, but also capable of obtaining a wide ranges of proteins that are not detectable by other means.

7 Claims, 2 Drawing Sheets

Cell Surface Protein Capture

- Chemically activate cell surface proteins on <u>intact</u> cells
    - Glycoproteins – cell surface
    - Periodate oxidation (→ aldehydes)
    - Galactose and sialic acid residues
- Capture glycoproteins on solid phase support
    - Covalent capture on hydrazide agarose
    - Stringent wash to remove non-covalent capture

SELECTIVE CAPTURE AND ENRICHMENT OF PROTEINS EXPRESSED ON THE CELL SURFACE

BACKGROUND

Cell surface glycoprotein plays a role in the interactions that regulate many important biological processes, from cell-cell adhesion to signal transduction. Glycosylation is very common and important post-translational modification of proteins and has a critical role in cell-cell communication and recognition. The majority of proteins are either O-glycosylated (at serine or threonine residues) or N-glycosylated (at asparagine residues). Several reports have indicated that glycosylation can be altered in cancerous cells (Dwek et al., Proteomics 1:756-762, 2001). Protein glycosylation is abundant in extracelllular environments. These proteins include proteins on the extracellular side of the plasma membrane, secreted proteins and proteins contained in body fluids such as blood serum, cerebrospinal fluid, urine, breast milk, saliva, lung lavage fluid or pancreatic juice.

Typically, cell surface proteins are transmembrane proteins with the carbohydrate moieties on the outside of the cells. The capture of cell membrane proteins using different chemistries (i.e. reaction with free sulfhydryl groups, lysine groups) has been described (Hoffman, Clinical Chemistry 46: 1478-1486, 2000).

Periodate oxidation was first disclosed by Spiro (Spiro and Bhoyroo, J. Biol. Chem. 249: 5704, 1974). The method is to oxidize the carbohydrate moieties on a protein such as a glycoprotein. Sialic acids are the most abundant terminal components of oligosaccharides on mammalian cell-surface glycoproteins and are synthesized from the six-carbon precursor N-acetylmannosamine.

It is also well known in the art that the most common method for introducing aldehydes and ketones into polysaccharides and glycoproteins is by periodate-mediated oxidation of vicinal diols. Periodate oxidation has been used to develop tagged specific cell populations (Molecular Probe, OR, Product list 3.2. Hydrazines and Aromatic Amines for Modifying Aldehydes and Ketones). The cell surface sialic acid-rich glycoprotein has been described to be labeled by periodate/$NaB_3H_4$ cell-surface labeling techniques (Spring et al, Biochem. J. 213:661-670, 1983). Moreover, periodate oxidation has been used for the oxidation of aldehyde groups on cell surface sialic acid at room temperature. Then these groups are used to ligate moieties onto the cell surface using hydrazides such as fluorescent hydrazide dye (Wood et al, European Cells and Mterials, 4, Suppl. 2:60-61, 2002.)

Cell surface proteins participate in sensing external signals and responding to environmental cues. Changes in the abundance of cell surface proteins can reflect a specific cellular state or the ability of a cell to respond to its changing environment. Therefore, the comprehensive, quantitative characterization of the protein components of the cell surface can identify marker proteins or a cluster of marker protein characteristics for a particular cellular state or explain the molecular basis for cellular responses to external stimuli. In many cases, changes in expression of a number of cell surface proteins such as Her2/Neu/erB, IGFI receptor and EFF receptor have been implicated in carcinogenesis and a current antibody therapy is based on targeting the cell surface protein Her2/neu receptor (Herceptin).

Isolated cell surface proteins depending upon enrichment of membranous subcellular fractions may result in substantial contamination with proteins that are localized to intracellular membranes (estimated to be around 15 to 30-fold more abundant than cell surface proteins). Other capture-based approaches rely upon the capture of cell surface proteins using non-covalent interactions. As this does not permit the stringent washing of immobilized proteins, a high degree of contamination occurs, which eliminates the empirical and broad identification and relative quantification of cell surface proteins. Therefore, it is important to obtain an enriched amount of pure cell surface protein, and to minimize "leaking" of cell content because numerous expressed proteins (present in the cytoplasm) are also glycosylated.

SUMMARY OF INVENTION

The present invention provides a method to capture cell surface proteins, with special emphasis on those that are differentially expressed in cancer cells. The method is able to chemically modify the carbohydrate moiety without destroying the cell membrane so as to capture the cell extracellular membrane components. This procedure yields over 50-100 or 100 fold or more enrichment of cell surface proteins relative to the total cellular protein complement, depending upon the cell type. The enriched proteins are typically composed of greater than 75% cell surface proteins. Unlike any other existing methodology to analyze the cell surface, the method of the present invention is capable of identifying proteins whose cell surface localization is previously not known or predicted.

The present invention provides a method for obtaining cell surface protein comprising the steps of: a) obtaining a biological sample, b) mixing the biological sample with periodate forming a mixture, c)reacting the mixture with a reagent forming a binding complex, and d) isolating the proteins from the binding complex, wherein the isolated proteins are cell surface proteins.

The present invention further provides that the biological samples are intact cells that are either cell lines or cells isolated from a tissue.

The present invention further provides that the periodate is a periodate salt, preferably sodium periodate.

The present invention further provides that the reagent is selected from a group consisting of hydrazide and amine. The binding reagent may be attached to a resin or a solid support to immobilize the proteins.

The present invention further comprises a washing step to separate glycosylated cell surface protein from other proteins. The binding complex is washed under a stringent condition.

The present invention provides that the cell surface proteins are 50-100 fold or 100 fold more enriched relative to total cellular proteins, depending on the cell type, preferably 100 fold enriched relative to total cellular proteins. The preferred cell types are epithelial cells either from normal or diseased tissues such as lung cancer.

The present invention further provides a method for obtaining cell surface proteins from a tissue sample comprising the steps of: a) obtaining a concentrated homogenous cell population from a tissue, which is an intact cell sample, b)mixing the sample with a periodate forming a mixture, c)reacting the mixture with a reagent forming a binding complex, and e)isolating the proteins from the binding complex, wherein the isolated proteins are cell surface proteins.

The present method further provides a binding complex comprising cell surface proteins of intact cells oxidized by periodate covalently bonded to a binding reagent that reacts to carbonyl groups of the cell surface proteins. The binding reagent is selected from a group consisting of hydrazide and amine, and preferably hydrazide. The binding reagent may also be attached to a solid phase or resin. The periodate is preferably sodium periodate.

The present invention further provides a method for obtaining an enriched amount of cell surface protein by the steps recited above. The cell surface proteins are from biological samples which include but are not limited to serum, body fluids, cells, tissues, organs or membrane extracts thereof.

DETAILED DESCRIPTION OF THE INVENTION

Figure 1:
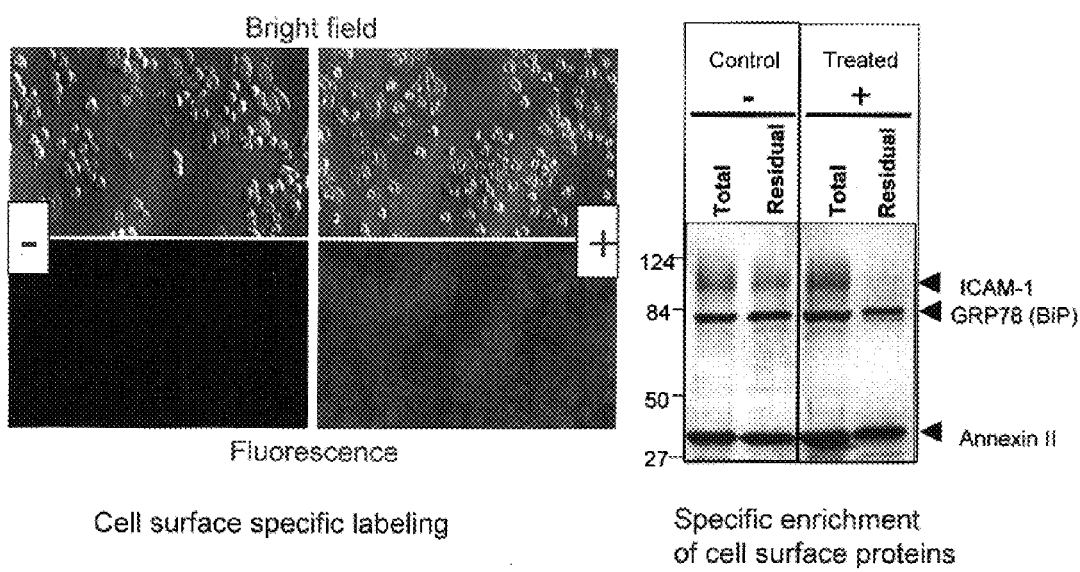
FIG. 1. Illustration of the cell capture process. Photographs show untreated cells(top left), periodate treated cells (top right), cells treated with a fluorescent hydrazide dye (lexafluor 488) (bottom left), and cells treated with periodate and subsequently reacted with a dye(bottom right). The left panel is a Western Blotting assay showing that after the treatment with periodate, the cell surface protein (ICAM-1) is depleted in the supernatant, which indicates that the ICAM-1 is captured.
Figure 2:
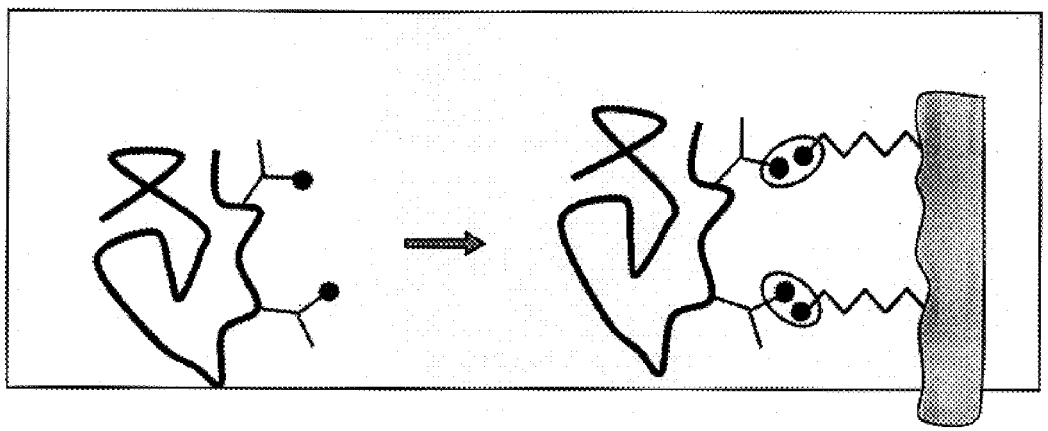
FIG. 2, Schematic illustration of cell surface protein capture

The cell surface proteins participate in sensing external signals and responding to environmental cues. Changes in the abundance of cell surface protein can reflect a specific cellular state or the ability of a cell to respond to its changing environment.

Thus, the comprehensive, quantitative characterization of the protein components of the cell surface can identify marker proteins or constellations of marker proteins characteristic for a particular cellular state, or explain the molecular basis for cellular responses to external stimuli.

Cell surface proteins are also experimentally accessible. Diagnostic assays for cell classification and preparative isolation of specific cells by methods such as cell sorting or panning are based on cell surface proteins. Thus, differential analysis of cell surface proteins between normal and diseased cells (e.g., cancer) can identify important diagnostic or therapeutic targets. While the importance of cell surface proteins for diagnosis and therapy of cancer has been recognized, membrane cell surface proteins have been difficult to analyze. Due to their generally poor solubility, they tend to be under-represented in standard 2D gel electrophoresis patterns and attempts to adapt 2D electrophoresis conditions to the separation of membrane proteins have met limited success. The method of this invention can overcome the limitations inherent in the traditional techniques.

Moreover, the analysis of membrane cell surface proteins is challenging because they generally are difficult to maintain in solution under conditions that are compatible with high-sensitivity analytical instruments such as mass spectrometers.

The application of the methods of the present invention to the analysis of membrane cell surface protein is exemplified using human pancreatic cell lines, human colorectal and lung cell lines and tissues (see Working Examples).

Because the vast majority of cell surface proteins are glycosylated, when exposed to an oxidant, vicinal hydroxyls on glycosyl residues are oxidized, which generate a carbonyl group. The present invention provides a method that by treating intact cells with sodium periodate, a reagent that does not traverse the cell membrane, glycosyl residues that are exposed to the extracellular milieu are oxidized to generate carbonyl groups. Because the cells are treated in such a way as to exclude the sodium periodate solution from the cell interior, the generation of carbonyls is limited to those glycoproteins on the cell surface and the abundant intracellular glycoproteins are not oxidized and in turn not captured. As carbonyl functional groups are rare in biological systems, the carbonyl-tagged cell surface glycoproteins can be specifically captured from total cell lysates through a coupling reaction with a hydrazide reactive group that is immobilized on a solid support or resin. This reaction yields a covalent hydrazone bond between the carbonyl moiety of the oxidized cell surface protein and the immobilized hydrazide group. This covalent attachment of cell surface glycoproteins to the resin allows stringent and vigorous washing of the loaded resin to efficiently eliminate non-covalently bound molecules that are associated with the resin in a non-specific manner. The proteins are subsequently recovered by reduction reagent. This procedure yields over 50-100 or 100-fold more enrichment of cell surface proteins relative to the total cellular protein complement, depending on the cell type. The enriched proteins are typically composed of greater than 75% cell surface proteins.

In addition to relative protein quantity and identity, the method can also be used to reveal the orientation of the protein in the membrane, based on the presumption that intact, live cells will exclude the oxidation reagent.

The present invention provides a method for obtaining cell surface proteins comprising the steps of: a) obtaining a biological sample, b) mixing the biological sample with a periodate forming a mixture, c)reacting the mixture with a reagent forming a binding complex, and d) isolating the proteins from the binding complex, wherein the isolated proteins are cell surface proteins.

As used herein, cell surface proteins are the exterior membrane and its associated proteins of a cell.

However, the present invention also encompasses proteins obtained from body fluids, sera or secreted proteins or cell membrane extract, whole cell extracts, which comprise enriched glycoprotein that can be a diagnostic marker or disease targets for immunotherapy or pharmacological intervention As used herein, biological samples encompass serum, biological fluids, cell membrane extracts, intact cells, tissues and organs, preferably intact cells or intact cell from tissues. Intact cell sample used herein is a whole cell sample preparation of whole cell without membrane disruption.

Generally, cell lines are grown in tissue culture media supplemented with cell type-specific growth supplements, which are known in the art. Cell media are changed every 48-72 hours. Cells are grown until 75-80% confluency and harvested for experimentation or expanding the culture using trypsin or versene. Cells are grown 24-48 hours in culture until the appropriate confluency prior to experimentation. The specific example is provided in the Working Example section.

In another embodiment, the cells are obtained from frozen or fresh tissues such as lung, colorectal, breast that are normal or cancerous tissues.

In yet another embodiment, an enriched amount of homogenous cells from tissues is also obtained by employing cell sorting techniques, which is known to one of ordinary skill in the art (eg. information provided by Becton, Dickinson and Company, BD Biosciences). The homogenous cell types used herein are the cells with the same type of classification, for example epithelial cells from either normal or cancerous tissues.

In yet another embodiment, cells are sorted using a flow cytometry high-speed sorter with a 70 uM nozzle 60 psi sheath pressure. The sort speed for cell enrichment is approximately $2 \times 10^7$ cells per hour. For sorting, cells are stained for 30 minutes with anti-CD45-FITC and anti-EpCAM-APC antibodies. A specific procedure is provided in the Working Example section.

The cells are further prepared for the oxidation process.

As used herein, periodate denotes the $IO_4^-$ ion present in aqueous solutions of periodic acid salts and in particular salts deriving from alkaline metals, preferably sodium periodate or potassium periodate. Said salts are also known as metaperiodates.

As used herein, a reagent that reacts with a carbonyl group of oxidized glycoprotein is either hydrazide or amine or related compounds that may be attached to the solid support or resin. The reagent forms a covalent bond to a hydrazide group and thereby is immobilized on a solid support or resin.

The periodate oxidation reaction by formation of carbonyl groups may be carried out at a moderately acid pH, preferably physiological conditions, such as between 5 and 8. The periodate is used in excess; more particularly, the concentration of alkali metal periodate is always greater than the concentration of vicinal diols capable of being oxidized: concentrations of 1 to 50 mM in respect of sodium periodate for concentrations of 1 to 10 mg/ml of cytotoxic sub-unit are suitable.

In one embodiment, cells in a single cell suspension from either cell lines or disassociated tissue specimens are processed for the membrane capture procedure. Cell number and viability are determined by propidium iodine (PI) exclusion (GUAVA). Cells are incubated for 10 minutes at 4° C., protected from light, with 1 mM sodium periodate. Cells are washed 3 times with D-PBS, lysed in a protein lysis buffer by vortexing, incubated for 1 hour at 4° C., and sheared through an 18-gauge needle. Protein concentration is determined using a DC protein assay (BioRad).

As used herein, a stringent condition is defined as using solutions containing high concentration salt buffer, organic solvent or detergent that are known to one of ordinary skill in the art. The preferred condition is to use strong chaotropic reagents that dissolve a biological sample by disrupting weak intermolecular forces like van der Waal's attractions. The chaotropic reagents include, but are not limited to guanidine salt such as guanidine hydrochloride, guanidinium thiocyanate, isothcyanate, sodium perchlorate, iodides, trifluroacetates, urea, trichloroacetates, alkali metal perchlorate and thiocyanates. For references see U.S. Pat. Nos. 5,593,824 and 5,244,577.

In one embodiment, the resin is washed with 80% ethanol, 8 M guanidine chloride (Pierce cat# 24115), and washed with another 80% ethanol, and stored in 80% ethanol for further biochemical sample processing.

In another embodiment, the resin is washed with 8 M guanidine HCl (6×), 80% ethanol (2×), 20% acetonitrile (6×), 80% ethanol (2×), and 5 urea in 0.1 M Tris, pH 8.0 (6×). Then 10.0 μL of 0.25 M DTT in 1.0 mL of 5 M urea with 0.1 M Tris, pH 8.0 is added for reduction, and the reaction mixture is incubated with rotation at 37° C. for one hour. After the reduction, the resin is washed twice with 5 M Urea in 0.1 M Tris, pH 8.0.

In yet anther embodiment, the resin is washed six times with an equal volume of urea solution (8 M urea/0.4 M $NH_4HCO_3$, pH8.3). The resin is diluted with 3 bed volumes of water and trypsin is added at a concentration of 1 ug of trypsin/200 ug of serum protein and digested at 37° C. overnight. The peptides are reduced by adding 8 mM TCEP at room temperature for 30 minutes. The trypsin-released peptides are removed by further washing as described above.

In one embodiment, the covalently bonded cell surface proteins are treated with reduction reagents, which include but are not limited to, tributylphosphine (TCEP), dithiothreitol/dithioerythritol (DTT), iodoacetic acid, iodoacetamide, 4-vinylpyridine, dimethylacrylamide, formic acid, hydrogen peroxide, N-isopropyliodoacetamide and N-ethylmorpholine, preferably DTT or TCEP.

The embodiment further comprises the step of alkylation of cysteines of reduced protein or peptide, and subsequently digests with enzyme particularly with proteases such as trypsin.

The yield of the proteins ranges 50 fold, 100 fold or 150 fold more relative to the total cellular proteins. In particular, in epithelial cell lines, the yield is at least about 100 fold enriched relative to total cellular proteins.

In one embodiment, the protein or peptide is alkylated with ICAT d0 (normal cell) or ICAT d8 (tumor cell), and digested with trypsin. The ICAT labeled cysteine-containing peptides were isolated using an avidin cartridge before LC/MS analysis.

Labeled amino acids of the covalently bonded cell surface proteins with isotopically labeled reagents are for subsequent analysis of differential expression.

WORKING EXAMPLES

1. Cell Culture

Pancreatic cell lines were grown in a culturing medium that is supplemented as necessary with growth factors and serum. Cultures were established from frozen stocks in which the cells were suspended in a freezing medium (cell culture medium with 10% DMSO [v/v]) and flash frozen in liquid nitrogen. Frozen stocks prepared in this way were stored in liquid nitrogen vapour. Cell cultures were established by rapidly thawing frozen stocks at 37° C. Thawed stock cultures were slowly transferred to a culture vessel containing a large volume of culture medium that was supplemented. For maintenance of the culture, cells were seeded at $1 \times 10^5$ cells/per ml in medium and incubated at 37° C. until confluence of cells in the culture vessel exceeded 50% by area. At this time, cells were harvested from the culture vessel using enzymes or EDTA when necessary. The density of harvested, viable cells was estimated by hemocytometry and the culture reseeded as above. A passage of this nature was repeated no more than 25 times at which point the culture was destroyed and reestablished from frozen stocks as described above. For the analysis of cell surface protein expression in cultured cell lines, cells were grown as described above. At a period 24 h prior to the experiment, the cell line was passaged as described above. This yielded cell densities that were <50% confluent and growing exponentially.

Lung cancer cell lines were obtained from ATCC. Cancer cell lines NCI-H23, NCI-H2291, NCI-H1299, NCI-H441, Calu-1, and Calu-3 were cultured in RPMI 1640 supplemented with 1×sodium pyruvate, 10% FBS, 10 mM Hepes, 1×penicillin-streptomycin-glutamine, and 1×non-essential amino acids. Cancer cell lines NCI-H522 and NCI-H358 were cultured in RPMI 1640 supplemented with 10% FBS, 10 mM Hepes, 1×penicillin-streptomycin-glutamine, and 1×non-essential amino acids. A549 was cultured in Ham's F12 media supplemented with 10% FBS, 1×penicillin-streptomycin-glutamine, and sodium bicarbonate. SK-LU-1 was cultured in D-MEM media supplemented with 10% FBS and 1×penicillin-streptomycin-glutamine. Non-cancer lung cell lines Beas-2B, Bet-1A, and HBE4-E6/E7 were purchased from ATCC. These cell lines were cultured in LHC-9 serum-free media supplemented with 1×penicillin-streptomycin-glutamine.

Primary normal human bronchial epithelial cells (NHBE) were obtained from Cambrex. NHBE cells were cultured in LHC-9 media. All cells were passaged twice a week. Cancer cells were disassociated with trypsin and the non-cancer cell lines and primary cells were disassociated with versene. Prior to harvesting for experiments, cells were cultured for 48 hours until 75-80% confluency and disassociated with versene. All tissue culture reagents were purchased from BioFluids.

2. Tissue Processing

Normal and tumor tissue is collected in the appropriate tissue transport buffer. Necrotic tumor tissue is removed and weight and dimension measurements of the tissue are taken. Tissue is disassociated by mechanical and enzymatic means to obtain a single cell suspension. Red blood cells are lysed with PharMLyse (BD Biosciences) when necessary. Cell number and viability are determined by PI exclusion (GUAVA). Cells at a total cell number greater than $20\times10^6$ are sorted using a high-speed sorter (MoFlo Cytomation) for epithelial cells (EPCAM positive).

Lung Transport Buffer was composed of LHC-9 media supplemented with 1×penicillin-streptomycin-glutamine, 1×fungizone (BioFluids) and Protease Inhibitor Cocktail (Sigma). Upon arrival, tissues were imaged, weighed, and dimensions measured (L×W×H). Tumor tissue was dissected when necessary for removal of necrotic regions. Tissue was re-weighed post-dissection.

Tissue was crudely minced and incubated for 20-30 minutes with periodic agitation at 37° C. in Enzyme Combination #1 (200 units Collagenase cat# C5894 Sigma; 126 ug DNAse 1 cat#D4513 Sigma in 10 mM Tris/HCl pH7.5; 50 mM NaCl; 10 mM MgCl2; 0.05% Elastase cat# E7885 Sigma). D-PBS was added at 3 times the volume of the enzyme combination, the tissue finely minced, and disassociated cells passed through a 200 um filter. The cells were washed twice with D-PBS.

The remaining undigested tissue was incubated for 20-30 minutes with periodic agitation at 37° C. in Enzyme Combination #2 (1× Liberase Blendzyme 1 cat# 988-417 Roche, 1× Liberase Blendzyme 3 cat#814-184 Roche, 0.05% Elastase cat# E7885 Sigma). D-PBS was added at 3 times the volume of the enzyme combination, the tissue finely minced until tissue completely disassociated. The cells were passed through a 200 um filter, washed twice with D-PBS, and pooled with cells from Enzyme Combination #1 digestion.

Cells were passed through a 70 um filter for single cell suspension and cell number and viability was determined by PI exclusion (GUAVA). When needed, red blood cells were lysed with PharMLyse (BD Biosciences). Cells were incubated in 20 ml of 1× PharMLyse in D-PBS for 30 seconds with gentle agitation and cells pelleted at 300 g for 5 minutes at 4° C. Cells were washed once in D-PBS and cell number and viability were recalculated by PI exclusion using the GUAVA. Cells at a total cell number greater than $20\times10^6$ were sorted using a high-speed sorter (MoFlo Cytomation) for epithelial cells (EpCAM positive).

3. Enrichment of Cells by Cell Sorting

Normal or tumor colorectal tissue was transferred from the transport vessel to a sterile dish containing 25 ml of ice-cold transport buffer. The tissue was measured, weighed and photographed. The tissue was dissected to isolate colorectal mucosa which was transferred to a fresh dish containing 25 ml ice-cold Hanks buffered saline solution. The tissue section was washed by vigorous shaking and the HBSS replaced. This was repeated twice or until all visible mucus was removed. Mucosa was measured, weighed and diced. The tissue sections were transferred to a 50 ml polypropylene centrifuge tube containing 50 ml of A52 media (Biosource) supplemented with 2 mM L-glutamine and 1.5 mg/ml dispase (Roche Biochemicals). The digest was incubated for 1 h at 37° C. with frequent agitation. Following the incubation, the suspension was poured through a 40-mesh cell sieve situated in the base of a 15 cm culture dish. The filtrate was diluted to 50 ml using A52 media supplemented with 2 mM L-glutamine and passed through a 200-mesh cell sieve. The filtrate was collected into a 50 ml polypropylene centrifuge tube and the suspension was triturated several times followed by vortexing for 2 min at setting 6. The density and viability of nucleated cells was determined by flow cytometry using propidium iodide as a negative stain for viability (Guava system). Erythrocytes were lysed using a standard ammonium chloride lysis protocol with incubation at room temperature for 10 s. Cells were harvested by centrifugation at 500 g for 5 min at 4° C. The cell pellet was resuspended in 50 ml of ice-cold HBSS and recentrifuged. The final cell pellet was resuspended in 3 ml of ice-cold HBSS supplemented with 0.1% BSA and 0.25 M EDTA. Cell density and viability were estimated using the Guava system and the density adjusted to $1\times10^7$ cells per ml. Epithelial cells were stained with a FITC-labeled anti-EpCAM murine monoclonal antibody and enriched by cell sorting using flow cytometry.

Cells isolated from lung tumor and normal tissue were resuspended in Sort Staining Buffer at a concentration of $2\times10^6$ cell/ml and labeled for 30 minutes with 20 ul/$10^6$ cells of anti-CD45-FITC (cat# 347463 BD Biosciences) and 5 ul/$10^6$ cells of anti-EpCAM-APC (cat# 347200 BD Biosciences). Cells were pelleted for 5 minutes at 300×g and washed once with Sort Staining Buffer. Cells were resuspended in Sort Staining Buffer at a concentration of $1\times10^7$ cells/ml. Cells were sorted using a high speed cell sorter with a 70 uM nozzle and 60 psi sheath pressure at a sort speed of approximately $2\times10^7$ cells per hour.

4. Periodate Oxidation

Cells in a single cell suspension from either cell lines or disassociated tissue specimens were processed for the membrane capture procedure. Cell number and viability were determined by propidium iodine (PI) exclusion (GUAVA). Cells were incubated for 10 minutes at 4° C. protected from light with 1 mM sodium periodate. Cells were washed 3 times with D-PBS, lysed in a protein lysis buffer by vortexing, incubated for 1 hour at 4° C., and sheared through an 18-gauge needle. Protein concentration was determined using a DC protein assay (BioRad).

Cultures were prepared as described above to yield approximately $1\times10^8$ cells. Culture medium was aspirated from each flask and the cell monolayer washed 3 times with 50 ml of ice-cold Dulbecco's phosphate buffered saline (no divalent cations; DPBS). Following the removal of the final DPBS wash, cells were exposed to 5 ml of versene for 5 min at 37° C. and harvested cells collected in a 50 ml polypropylene centrifuge tube. Cells were triturated and cell density and viability estimated by hemocytometry using vital dyes. Cells were centrifuged at 500×g at 4° C. for 5 min and the cell pellet resuspended at an estimated density of $1\times10^7$ cells/ml.

Sodium metaperiodate was added to a final concentration of 1 mM and the cell suspension was incubated on ice for 10 min with frequent agitation in the dark. Cells were centrifuged at 500×g at 4° C. for 5 min and resuspended in 50 ml of ice-cold DPBS. The cell suspension was washed by 2 further cycles of centrifugation at 500×g at 4° C. for 5 min and resuspension of the cell pellet in 50 ml of ice-cold DPBS. Finally, the cell pellet was resuspended in lysis buffer (1% SDS [w/v]; 0.1 M HEPES; 10 mM $MgCl_2$; 0.1% Non ionic detergent P40; 10 ul/ml protease inhibitor cocktail [P8340, Sigma]) and homogenized by passage of lysate through a 18 G syringe needle 10 times. Protein concentrations were assayed relative to a Bovine Serum Albumin standard by a modified Lowry assay (DC assay, BioRAD), with 5 mg of total cellular protein transferred to a fresh tube and diluted to 1 mg/ml in acetate buffer (0.1M, pH 5.0). Meanwhile, 1 ml of hydrated adipic acid hydrazide agarose resin was equilibrated in 0.1 M acetate buffer (pH 5.0) by incubation at 4° C. for 3 h on a rotating platform. This is followed by 3 successive wash cycles of centrifugation at 3000 rpm for 3 min at 4° C. in a Sorvall HS4 rotor and resuspension in 50 mL of 0.1M acetate buffer (pH 5.0). The final resin pellet was resuspended in the 1 mg/ml protein solution and oxidized glycoproteins were immobilized by incubating overnight at 4° C. on a rotating platform in the dark.

The supernatant containing soluble proteins was collect and stored at −80° C. The resin was washed with 80% ethanol, 8 M guanidine chloride (Pierce cat# 24115), and another 80% ethanol, and stored in 80% ethanol for further biochemical sample processing. Alternatively, the resin was washed with 8 M guanidine HCl (6×), 80% ethanol (2×), 20% acetonitrile (6×), 80% ethanol (2×), and 5 urea in 0.1 M Tris, pH 8.0 (6×). Then 10.0 μL of 0.25 M DTT in 1.0 mL of 5 M urea with 0.1 M Tris, pH 8.0 was added for reduction, and the reaction mixture was incubated with rotation at 37° C. for one hour. After the reduction, the resin was washed twice with 5 M Urea in 0.1 M Tris, pH 8.0.

5. Flow Cytometry Confirmation of Membrane Capture

Cells from one T150 flask of tissue cultured lung cells were disassociated from the flask with versene. Cell number and viability determined by PI exclusion (GUAVA). A minimum of $2\times10^6$ cells were used for this experiment. Cells were incubated with 1 mM sodium meta-periodatde for 10 minutes at 4° C. protected from light. Cells were washed three times with PBS and incubated with 1 mM biotinamidocaporyl hydrazide for 30 minutes at room temperature. Cells were washed twice with PBS and incubated at 4° C. for 15 minutes with 10 ug of FITC-avidin. Cells were washed twice with PBS and incubated with propidium iodine (PI) at a concentration of 0.25 ug/ml. Cells analyzed on a LSR flow cytometry instrument (FIG. 1).

6. Analysis of Cell Surface Protein

Cell Line Samples:

Following the cell surface protein capture, the resin (stored in 80% ethanol) was transferred and packed into a 2.0 ml BioSpin disposable chromatography column. The resin was washed with 8 M guanidine HCl (6×), 80% ethanol (2×), 20% acetonitrile (6×), 80% ethanol (2×), and 5 urea in 0.1 M Tris, pH 8.0 (6×). Then 10.0 μL of 0.25 M DTT in 1.0 mL of 5 M urea with 0.1 M Tris, pH 8.0 was added for reduction, and the reaction mixture was incubated with rotation at 37° C. for one hour. After the reduction, the resin was washed twice with 5 M Urea in 0.1 M Tris, pH 8.0.

Five units of ICAT d0 (normal cell)/or ICAT d8 (tumor cell) was reconstituted in 1.0 mL 5 M urea in 0.1 M Tris, pH 8.0, and was transferred to the column for alkylation. The resin was incubated with rotation and protected from light at room temperature for one hour. The resin was washed twice with 5 M urea in 0.1 M Tris, pH 8.0, and 6 times with 50 mM $CaCl_2$ in 0.1 M Tris pH 8.0 in 10% acetonitrile. Ten μg of trypsin was added with 1.0 ml of 50 mM $CaCl_2$ in 0.1 M Tris pH 8.0 in 10% acetonitrile. The resin was incubated with rotation at 37° C. overnight. The eluant was collected into a 2 mL tube. The resin was washed once with 1 mL of 0.1 M Tris, pH 8.0 in 10% acetonitrile, and the eluant from this wash was collected. The collected eluant of ICAT d0 and ICAT d8 labeled peptide were combined and were diluted with 8.0 mL of 100 mM Tris, pH 8.0. A reversed phase Oasis cartridge was subsequently conditioned with MeOH, 70% acetonitrile containing 0.1% TFA, and twice with 0.1% TFA. The peptide solution was loaded in a conditioned Oasis cartridge. The cartridge was washed twice with 0.1% aqueous TFA. The peptides were eluted from the Oasis cartridge with 1.0 mL of 70% acetonitrile containing 0.1% TFA. The peptide fraction was evaporated to dryness and reconstituted in 200 mL of 50% acetonitrile, diluted with 800 uL of 2× PBS. The sample was injected on an HPLC (Vision) system to isolate the labeled peptides using a tandem column system composed of an avidin and an R2/10 tandem column. The fraction containing the ICAT labeled peptides was evaporated to dryness prior to MS analysis.

Tissue Samples

A similar process was developed using reducing reagents to accommodate a smaller sample size. Following up the cell surface protein capture, the resin stored in 80% ethanol was transferred and packed into a 750 mL BioSpin disposable chromatography column. Resin was washed with 8 M guanidine HCl (6×), 80% ethanol (2×), 20% acetonitrile (6×), 80% ethanol (2×), and 5 M urea in 0.1M Tris, pH 8.0 (6×). To the resin was added 2.0 mL of 0.25 M DTT in 300 mL of 5 M urea in 0.1 M Tris, pH8.0 to reduce the glycoproteins, and the reaction mixture was incubated with rotation at 37° C. for one hour. After the reduction, the resin was washed three times with 5.0 M urea in 0.1 M Tris, pH8.0. Two units of either ICAT d0 (normal cell)/or ICAT d8 (tumor cell) were reconstituted in 300 uL of 5 M urea in 0.1 M Tris, pH8.0, and were transferred to the column for alkylation. The resin was incubated with rotation and protected from light at room temperature for one hour. Afterwards, the resin was washed twice with 5.0 M urea in 0.1 M Tris, pH8.0, and 6 times with 0.1 M $NH_4HCO_3$ (pH 8) in 10% Acetonitrile. Acetylated trypsin (5 mg) was added with 300 mL of 0.1 M $NH_4HCO_3$ (pH 8) in 10% acetonitrile. The resin was incubated with rotation at 37° C. overnight. The eluant was collected into a 2 mL tube. The resin was washed once with 300 uL of (0.1 M $NH_4HCO_3$, pH 8.0) in 10% acetonitrile, and the eluant was collected. The peptides were dried for 2.5 hours in the Gen-Vac and reconstituted with 20 mL of 25% acetonitrile. The peptide solution was diluted with 80 uL of 2×PBS. Trypsin inhibitor pefabloc (2.5 mL, 20 mM) was added into this reconstituted solution. Samples were injected on an Agilent HPLC system to capture the cysteine-containing peptides using avidin and R2/10 columns in tandem. The collected fractions were dried for MS analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of protein chemistry, molecular biology or related fields, are intended to be within the scope of the following claims.

That which is claimed is:

1. A method for obtaining cell surface proteins comprising the steps of:
   a) mixing intact cell sample with a periodate forming a mixture,
   b) reacting the mixture with a reagent forming a binding complex, and wherein the reagent is selected from a group consisting of hydrazide and amine,
   c) isolating the proteins with a reduction reagent from the binding complex, wherein the isolated proteins in the reduction reagent are cell surface protein.

2. The method of claim 1, wherein the intact cells are either cell lines or cells isolated from tissues.

3. The method of claim 1, wherein periodate is sodium periodate.

4. The method of claim 1, wherein the binding reagent is on a resin or a solid support.

5. The method of claim 1, wherein the cell surface proteins are 50 folds enriched relative to the total cellular proteins.

6. The method of claim 1, wherein the cell surface proteins are 100 folds enriched relative to the total cellular proteins.

7. A method for obtaining cell surface proteins comprising the steps of:
   a) obtaining a homogenous cell population from a biological samples, which are intact cell,
   b) mixing intact cell sample with a periodate forming a mixture,
   c) reacting the mixture with a reagent forming a binding complex, and wherein the reagent is selected from a group consisting of hydrazide and amine,
   d) isolating the proteins with a reduction reagent from the binding complex, wherein the isolated proteins in the reduction reagent are cell surface protein.

* * * * *